United States Patent [19]

Kondo et al.

[11] Patent Number: 5,340,683

[45] Date of Patent: Aug. 23, 1994

[54] PRESENSITIZED PLATE HAVING SURFACE-GRAINED AND ANODIZED ALUMINUM SUBSTRATE WITH LIGHT-SENSITIVE LAYER CONTAINING QUINONE DIAZIDE SULFONIC ACID ESTER OF PARTICULAR POLYHYDROXY COMPOUND

[75] Inventors: Syunichi Kondo; Akira Nagashima; Yasumasa Kawabe, all of Shizuoka, Japan

[73] Assignee: Fuji Photo Film Co., Ltd., Minami-Ashigara, Japan

[21] Appl. No.: 86,864

[22] Filed: Jul. 7, 1993

[30] Foreign Application Priority Data

Jul. 22, 1992 [JP] Japan .................. 4-195619

[51] Int. Cl.$^5$ .................. G03F 7/023; G03F 7/09
[52] U.S. Cl. .................. 430/165; 430/191; 430/192; 430/193; 430/278; 430/302
[58] Field of Search .............. 430/165, 192, 193, 278, 430/191; 534/556, 557, 558

[56] References Cited

U.S. PATENT DOCUMENTS

| | | | |
|---|---|---|---|
| 4,719,167 | 1/1988 | Miura et al. | 534/557 |
| 5,153,096 | 10/1992 | Uenishi et al. | 430/193 |
| 5,198,322 | 3/1993 | Wilharm et al. | 430/193 |

FOREIGN PATENT DOCUMENTS 443820 8/1991 European Pat. Off. .

*Primary Examiner*—Charles L. Bowers, Jr.
*Assistant Examiner*—Christopher G. Young
*Attorney, Agent, or Firm*—Burns, Doane, Swecker & Mathis

[57] ABSTRACT

A PS plate comprises a surface-grained and anodized aluminum plate provided thereon with a light-sensitive layer of a composition comprising a light-sensitive substance and an alkali-soluble resin wherein the light-sensitive substance is a 1,2-naphthoquinonediazide-5- (or -4-) sulfonic acid ester of a polyhydroxy compound of formula (I):

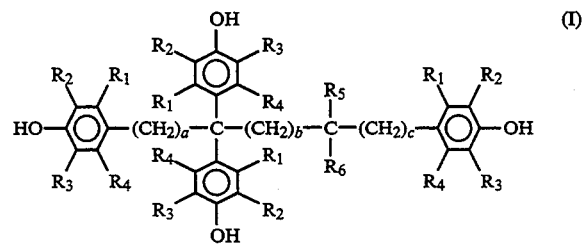

wherein substituents $R_1$ to $R_4$ may be same or different and each represents a hydrogen atom, a hydroxyl group, a halogen atom, an alkyl group, an alkoxy group or an alkenyl group; $R_5$ and $R_6$ each represents a hydrogen atom, an alkyl group or a group:

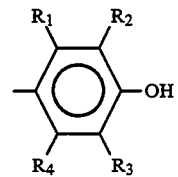

a and c each represents 0–1 and b represents 0–4. The PS plate permits the complete removal of any pasting mark and has a high development latitude.

9 Claims, No Drawings

PRESENSITIZED PLATE HAVING SURFACE-GRAINED AND ANODIZED ALUMINUM SUBSTRATE WITH LIGHT-SENSITIVE LAYER CONTAINING QUINONE DIAZIDE SULFONIC ACID ESTER OF PARTICULAR POLYHYDROXY COMPOUND

BACKGROUND OF THE INVENTION

The present invention relates to a presensitized plate for use in making a lithographic printing plate (hereinafter referred to as "PS plate" and more specifically to a PS plate comprising a specific o-naphthoquinonediazide compound.

There have been widely used aluminum plates as substrates for lithographic printing plates. These aluminum plates are surface-treated for improving the hydrophilicity and water-retention characteristics of the plates, for improving the adhesion thereof to image areas and for improving the strength of non-image areas of the resulting PS plates. These aluminum plates have been surface-treated by, for instance, mechanical surface-roughening treatments such as ball graining, wire graining and brush graining; electrolytic surface-roughening treatments by passing a DC or AC current through the aluminum plates in a hydrochloric acid or nitric acid bath; or any combination thereof. After the surface-treatment, these aluminum plates are anodized in a sulfuric acid or phosphoric acid bath.

The aluminum plate may optionally be subjected to sealing treatment with a silicate or hot water and/or to a dipping treatment in, for instance, a polyvinylsulfonic acid solution. It has been well-known that a PS plate is prepared by applying, onto the aluminum substrate thus prepared, a light-sensitive composition comprising an o-naphthoquinonediazide as a light-sensitive compound and a binder such as a novolak resin, vinyl resin or urethane resin.

In addition, it has already been known that the use of a reaction product of a polyhydroxy compound with an o-naphthoquinonediazide compound such as an o-naphthoquinonediazide light-sensitive compound permits, for instance, the inhibition of crystal-deposition in the resulting light-sensitive layer and the improvement of storability, adhesion to an aluminum substrate, and the chemical resistance and developability of the light-sensitive layer.

Examples of light-sensitive compositions containing such reaction products include those comprising o-naphthoquinonediazidesulfonic acid esters of polycondensed resins of pyrogallol and acetone as disclosed in Japanese Patent Publication for Opposition Purpose (hereinafter referred to as "J. P. KOKOKU") No. Sho 43-28403 (=U.S. Pat. No. 3,635,704); those comprising o-naphthoquinonediazidesulfonic acid esters of polycondensed resins of pyrogallol/resorcin mixture with acetone for controlling the developability of the resulting light-sensitive layer as disclosed in Japanese Unexamined Patent Publication (hereinafter referred to as "J. P. KOKAI") No. Sho 55-76346; and those comprising polycondensed resins of polyhydric phenols with benzaldehyde or acetaldehyde for improving the developability and chemical resistance of the resulting light-sensitive layer as disclosed in J. P. KOKAI Nos. Sho 50-1044 and Sho 50-1045.

However, the following problems have become evident after conducting various studies using these o-naphthoquinonediazidesulfonic acid esters of these polycondensed resins of polyhydroxy phenols with ketones or aldehydes.

A positive-working lithographic printing plate is, in general, prepared by pasting a plurality of original films carrying various pictures, patterns and/or characters on a transparent base to form a positive film, putting the film on the light-sensitive layer of a PS plate, exposing the assembly to ultraviolet rays and then developing the exposed PS plate with a developer. If the resulting lithographic printing plate requires highly improved printing durability, the plate is then subjected to a burning treatment to thermally harden the light-sensitive layer on the image area thereof. When the foregoing positive film is put on a light-sensitive layer comprising a conventional o-naphthoquinonediazidesulfonic acid ester of a polycondensed resin of a polyhydroxy phenol with a ketone or an aldehyde and then the assembly is exposed to light, however, the light-sensitive layer behind the edge portion of various original films pasted on the base film of the positive film used remains on the plate in a semi-exposed state. The semi-exposed light-sensitive layer is strongly adhered to the plate surface, cannot easily be removed with a developer and thus remains unremoved even after the completion of the development. The use of the resulting printing plate in printing operations results in background contamination of copies. The pasting marks thus formed on the exposed PS plate cannot completely be removed with a so-called non-toxic erasing solution (free of hydrofluoric acid as a violet poison) generally used for the treatment of positive-working PS plates. The pasting marks become more conspicuous when the plate is subjected to a burning treatment commonly used for improving the printing durability of the resulting lithographic printing plate and accordingly, the resulting printing plate cannot be used in printing operations.

Nevertheless, the light-sensitive layer comprising a conventional o-naphthoquinonediazidesulfonic acid ester of a polycondensed resin of a polyhydroxy phenol with a ketone or an aldehyde never suffers from such a trouble that the layer on the image portion is dissolved out in a developer having a high concentration, unlike those comprising other known o-naphthoquinonediazidesulfonic acid esters of 2,3,4,4'-tetrahydroxybenzophenone or phenols such as m-cresol). More specifically, the light-sensitive layer exhibits an advantage in that it has a wide development latitude.

SUMMARY OF THE INVENTION

Accordingly, an object of the present invention is to provide a PS plate or a lithographic printing plate whose pasting marks can be removed with an erasing solution free of harmful hydrofluoric acid and any ink does not adhere to the portions on which pasting marks are formed during imagewise exposure even after the plate is subjected to a burning treatment.

Another object of the present invention is to provide a PS plate having a wide development latitude.

The inventors of this invention have conducted various studies to accomplish the foregoing objects, have found out that the foregoing drawbacks associated with the conventional PS plates can completely be eliminated through the use of a specific light-sensitive substance and thus have completed the present invention.

The foregoing object of the present invention can effectively be accomplished by providing a PS plate which comprises a surface grained and anodized aluminum plate provided thereon with a light-sensitive layer of a composition comprising at least one light-sensitive substance and an alkali-soluble resin wherein the light-sensitive substance is a 1,2 (and/or 2,1)-naphthoquinonediazide-5- (and/or -4-)sulfonic acid ester of a polyhydroxy compound represented by the following general formula (I):

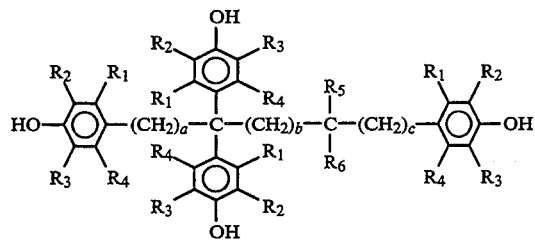

wherein substituents $R_1$ to $R_4$ may be the same or different and each represents a hydrogen atom, a hydroxyl group, a halogen atom, an alkyl group, an alkoxy group or an alkenyl group; $R_5$ and $R_6$ each represents a hydrogen atom, an alkyl group or a group:

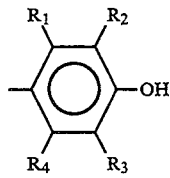

(wherein $R_1$ to $R_4$ are the same as those defined above), a and c each represents 0 or 1 and b represents 0 or an integer ranging from 1 to 4.

DESCRIPTION OF THE PREFERRED EMBODIMENTS

The present invention will hereinafter be described in more detail.

The PS plate of the present invention comprises at least one light-sensitive compound of Formula (I). In respect of the substituents $R_1$ to $R_4$ of Formula (I), preferred halogen atoms are chlorine, bromine and iodine atoms; preferred alkyl groups are those having 1 to 4 carbon atoms such as methyl, ethyl, propyl, n-butyl, isobutyl, sec-butyl and t-butyl groups; preferred alkoxy groups are those having 1 to 4 carbon atoms such as methoxy, ethoxy, hydroxyethoxy, propoxy, hydroxypropoxy, isopropoxy, n-butoxy, isobutoxy, sec-butoxy and t-butoxy groups; and preferred alkenyl groups are those having 1 to 4 carbon atoms such as vinyl, propenyl, allyl and butenyl groups.

Regarding the substituents $R_5$ and $R_6$ of Formula (I), the preferred alkyl groups are the same as those defined above in connection with the substituents $R_1$ to $R_4$.

The compounds represented by Formula (I) can be prepared by reacting carbonyl precursors with phenol derivatives, i.e., p-hydroxyphenyl ketone compounds (produced by, for instance, the method disclosed in Chemishe Berichte, 1941, 74, p. 1772) under acidic or alkaline conditions according to the method disclosed U.S. Pat. No. 4,426,513.

Moreover, they can be prepared through reactions of haloketone compounds with phenol derivatives under acidic conditions according to, for instance, the method disclosed in U.S. Pat. No. 2,965,611.

When the reaction is performed under an acidic condition, a mercapto group-containing compound is preferably used as a catalyst and specific examples thereof include ethanethiol, 1-butanethiol, thiophenol and mercaptoacetic acid.

It is preferred to perform the condensation reaction in the presence of stoichiometrically excess of the phenol component. The reaction temperature preferably ranges from room temperature to 100° C. or higher.

The progress of the condensation reaction can be monitored by a chromatographic or spectrophotometric means. For instance, it can easily be monitored by detecting reduction in the absorption band ascribed to carbonyl groups using IR spectrometric analysis.

These compounds can be purified by various purification techniques commonly used such as recrystallization and elution chromatography.

Solvents suitably used in the recrystallization thereof are, for instance, methylene chloride, benzene, cyclohexane, methanol, ethanol and alcohol-water mixture.

Optimally, the elution chromatography is carried out using alumina or silica as a fixed phase and a variety of solvents as eluents.

Specific examples of the compounds of Formula (I) prepared in the foregoing manner are those listed below as compounds [I-a] to [I-p], but the present invention is not restricted to these specific compounds.

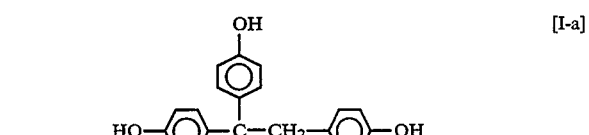
[I-a]

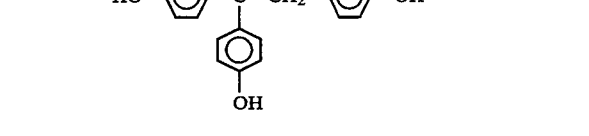
[I-b]

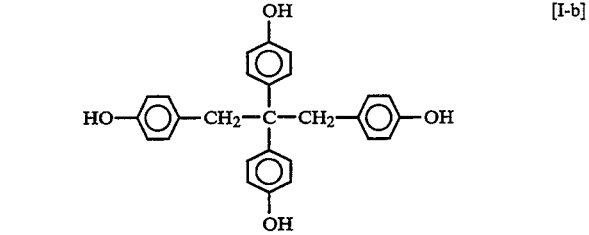
[I-c]

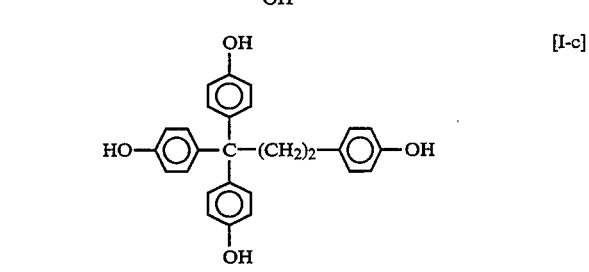
[I-d]

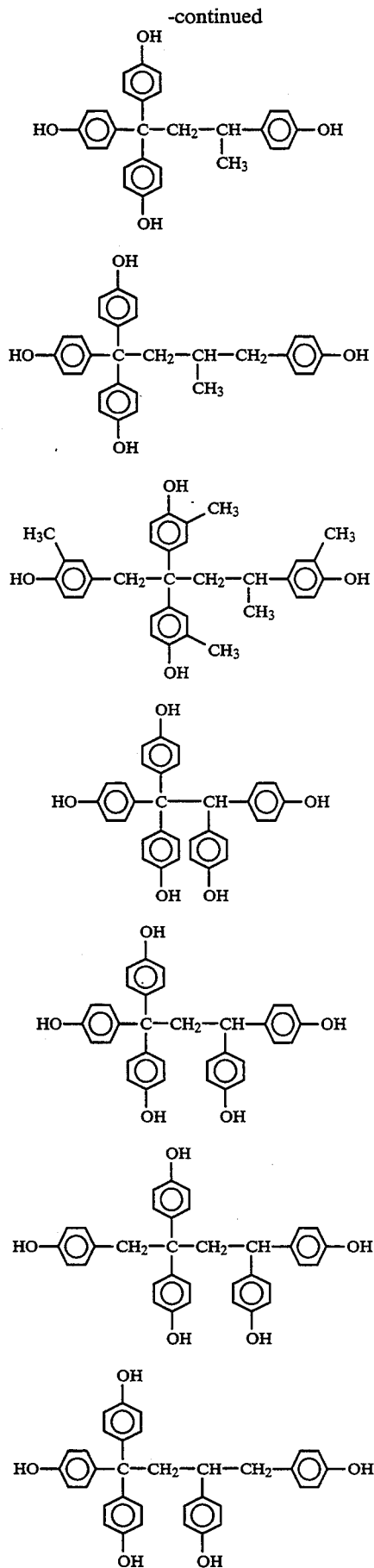

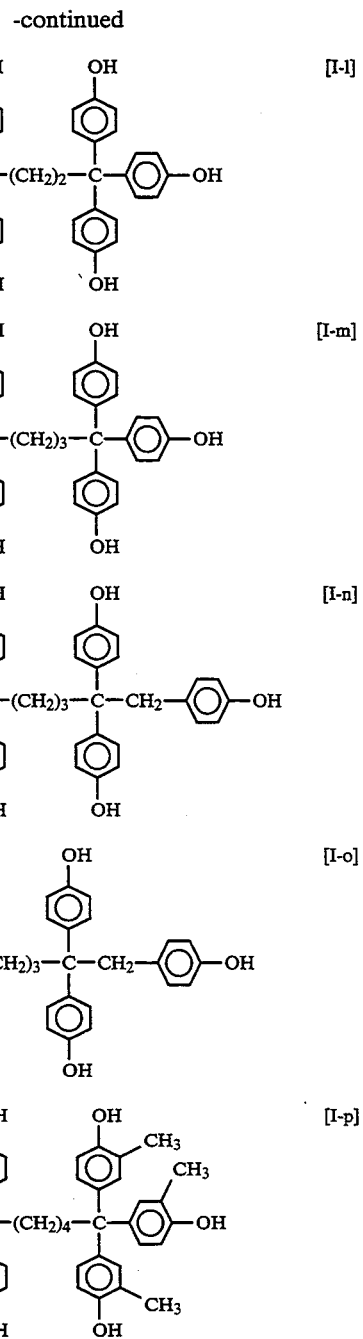

SYNETHSIS EXAMPLE 1

Synthesis of Compound [I-b]

Phenol (188 g; 2.0 mol) was added to dichloroacetone (25.4 g; 0.20 mol) and the mixture was heated to 45° C. to which hydrogen chloride gas was introduced. When the reaction mixture turned yellow, the heating was stopped and hydrogen gas was introduced for additional two hours. Then, red-brown reaction mixture was distilled under reduced pressure to remove excess phenol. The red-brown solid residue thus prepared was washed with n-hexane and purified on column chromatography (silica gel; eluent: n-hexane/ethyl acetate=2/1) to obtain 72 g of white powder. NMR analysis confirmed that the powder was 1, 2, 2, 3-tetrakis(4'-hydroxyphenyl)propane [I-b].

The light-sensitive substance used in the present invention can be prepared by partially or completely esterifying, in the usual manner, the hydroxyl groups on the foregoing polyhydroxy compound in the presence of 1, 2-naphthoquinonediazide-5-sulfonyl chloride and a basic catalyst.

More specifically, there are introduced, into a flask, desired amounts of a polyhydroxy compound and 1, 2-naphthoquinonediazide-5-sulfonyl chloride together with a solvent selected from the group consisting of, for instance, dioxane, acetone, methyl ethyl ketone and N-methylpyrrolidone and then a basic catalyst such as sodium hydroxide, sodium bicarbonate or triethylamine is dropwise added to the mixture to perform the condensation of the compounds. The resulting product is washed with water, purified and finally dried.

The foregoing esterification reaction results in the formation of a mixture comprising various esterified products whose degree of esterification and esterified positions differ from one another. For this reason, the term "degree of esterification" herein used is defined to be the average of the various esterified products.

The degree of esterification defined above can be controlled by adjusting the mixing ratio of these starting materials: polyhydroxy compound/1, 2-naphthoquinonediazide-5-sulfonyl chloride. In other words, all of 1, 2-naphthoquinonediazide-5-sulfonyl chloride added substantially undergoes esterification reaction and accordingly, a mixture having a desired degree of esterification can be prepared by appropriately controlling the molar ratio of the starting materials.

The foregoing polyhydroxy compounds may be reacted with other sulfonyl chlorides such as 2, 1-naphthoquinonediazide-5-sulfonyl chloride and 1, 2-naphthoquinonediazide-4-sulfonyl chloride in the same manner used above to give other light-sensitive substances usable in the present invention.

The reaction temperature in the foregoing method generally ranges from $-20°$ to $60°$ C. and preferably $0°$ to $40°$ C.

SYNETHSIS EXAMPLE 2

Synthesis of Light-sensitive Compound 1, 2, 2, 3-Tetrakis(4'-hydroxyphenyl)propane (41.2 g) prepared in Synthesis Example 1, 1, 2-naphthoquinonediazide-5-sulfonyl chloride (80.6 g) and acetone (600 ml) were charged in a three necked flask and dissolved homogeneously. Triethylamine/acetone (31.9 g/100 ml) were gradually dropped and reacted at 25° C. for three hours. The reaction mixture was poured into 3000 ml of 1% aqueous hydrochloric acid solution. The precipitate was filtered, washed with water and dried at 40° C. to obtain 1, 2-naphthoquinonediazide-5-sulfonic acid ester of 1, 2, 2, 3-tetrakis(4'-hydroxyphenyl)propane (78.0 g) (light-sensitive substance).

One or more of the light-sensitive compounds of the present invention prepared by the foregoing method may be incorporated into, for instance, an alkali-soluble resin to give a light-sensitive resin composition. In this respect, the amount of the light-sensitive compound to be incorporated ranges from 5 to 100 parts by weight and preferably 10 to 50 parts by weight on the basis of the total amount of the alkali-soluble resin. This is because if the amount thereof is less than 5 parts by weight, the rate of remaining film is substantially reduced, while if it exceeds 100 parts by weight, the resulting resin composition has low sensitivity and low solubility in a solvent.

The resin composition may optionally comprise other known light-sensitive substances in addition to those discussed above. Examples of these known light-sensitive substances include esters of 1, 2-diazonaphthoquinonesulfonic acid chloride with pyrogallol-acetone resins disclosed in U.S. Pat. No. 3,635,709; esters of 1, 2-diazonaphthoquinone-5-sulfonic acid chloride with phenol-formaldehyde resins disclosed in U.S. Pat. Nos. 3,046,120 and 3,188,210; esters of 1, 2-diazoquinone-4-sulfonic acid chloride with phenol-formaldehyde resins disclosed in J. P. KOKAI Nos. Hei 2-96163, Hei 2-96165 and Hei 2-96761; and those disclosed in, for instance, J. P. KOKAI Nos. Sho 47-5303, Sho 48-63802, Sho 48-63803, Sho 48-96575, Sho 49-38701 and Sho 48-13354, J. P. KOKOKU Nos. Sho 37-18015, Sho 41-11222, Sho 45-9610 and Sho 49-17481, U.S. Pat. Nos. 2,797,213, 3,454,400, 3,544,323, 3,573,917, 3,674,495 and 3,785,825; U.K. Patent Nos. 1,227,602, 1,251,345, 1,267,005, 1,329,888 and 1,330,932; and German Patent No. 854,890.

In this case, these known light-sensitive substances may be used in an amount of 1 to 100 parts by weight and preferably 5 to 30 parts by weight per 100 parts by weight of the light-sensitive substance of the present invention.

The alkali-soluble resins used in the present invention may be a variety of resins having desired properties, but preferred are novolak resins listed below:

Examples of such novolak resins usable in the invention include phenol/formaldehyde resins; and cresol/formaldehyde resins such as m-cresol/formaldehyde resins, p-cresol/formaldehyde resins, 0-cresol/formaldehyde resina, m-/p-mixed cresol/formaldehyde resins and phenol/mixed cresol (m-/ p-/ o-, m-/p- or m-/o- mixed cresol)/formaldehyde resins. In addition, resol type phenol resins are likewise suitably used. Preferred are phenol/cresol (m-/ p-/ o-, m-/p- or m-/o- mixed cresol)/formaldehyde resins, with phenol resins disclosed in J. P. KOKAI Nos. Sho 61-217034 being particularly preferred.

Furthermore, other various alkali-soluble polymeric compounds may likewise be used in the invention and examples thereof include phenol-modified xylene resins, polyhydroxy styrene, polyhalogenated hydroxystyrene, phenolic hydroxyl group-containing acrylic resins as disclosed in J. P. KOKAI No. Sho 51-34711, sulfonamido group-containing acrylic resins disclosed in U.S. Pat. No. 5,141,838 and urethane resins. These alkali-soluble polymeric compounds preferably have weight-average molecular weights ranging from 500 to 20,000 and number-average molecular weight ranging from 200 to 6,000.

These alkali-soluble polymeric compounds may be used separately or in combination in an amount of not more than 80% by weight on the basis of the total weight of the light-sensitive resin composition.

Moreover, it is preferred for the improvement of the ink receptivity of images to simultaneously use condensates of formaldehyde with phenols carrying, as substituents, alkyl groups having 3 to 8 carbon atoms such as t-butylphenol-formaldehyde resins and octylphenol-formaldehyde resins as disclosed in U.S. Pat. No. 4,123,279.

The light-sensitive composition used in the invention preferably comprises, for the improvement of sensitivity, cyclic acid anhydrides, phenols and/or organic acids. Examples of such cyclic acid anhydrides are phthalic anhydride, tetrahydrophthalic anhydride, hexahydrophthalic anhydride, 3,6-endoxy-Δ⁴-tetrahydrophthalic anhydride, tetrachlorophthalic anhydride, maleic anhydride, chloromaleic anhydride, α-phenylmaleic anhydride, succinic anhydride and pyromellitic anhydride. Such phenols include, for instance, bisphenol A, p-nitrophenol, p-ethoxyphenol, 2,3,4-trihydroxybenzophenone, 4-hydroxybenzophenone, 2,4,4'-trihydroxybenzophenone, 4,4',4''-trihydroxy-triphenylmethane and 4,4',3'',4''-tetrahydroxy-3,5,3',5'-tetramethyltriphenylmethane. Such organic acids are, for instance, sulfonic acids, sulfinic acids, alkylsulfuric acids, phosphonic acids, phosphinic acids, phosphoric acid esters and carboxylic acids as disclosed in J.P. KOKAI Nos. Sho 60-88942 and Hei 2-96755 and specific examples thereof are p-toluenesulfonic acid, dodecylbenzenesulfonic acid, p-toluenesulfinic acid, ethylsulfuric acid, phenylphosphonic acid, phenylphosphinic acid, phenyl phosphate, diphenyl phosphate, benzoic acid, isophthalic acid, adipic acid, p-toluylic acid, 3,4-dimethoxybenzoic acid, phthalic acid, terephthalic acid, 1,4-cyclohexene-2,2-dicarboxylic acid, erucic acid, lauric acid, n-undecanoic acid and ascorbic acid.

The content of the foregoing cyclic acid anhydrides, phenols and/or organic acids in the light-sensitive composition preferably ranges from 0.05 to 15% by weight and more preferably 0.1 to 5% by weight on the basis of the total weight of the composition.

The light-sensitive composition used in the invention may further comprise, for extending the development latitude, non-ionic surfactants as disclosed in J.P. KOKAI Nos. Sho 62-251740 and Hei 4-68355; and amphoteric surfactants as disclosed in J.P. KOKAI Nos. Sho 59-121044 and Hei 4-13149. Specific examples of non-ionic surfactants are sorbitan tristearate, sorbitan monopalmitate, sorbitan trioleate, stearyl monoglyceride, polyoxyethylene sorbitan monooleate and polyoxyethylene nonylphenyl ether and examples of amphoteric surfactants are alkyl di(aminoethyl)glycine, alkyl polyaminoethyl glycine hydrochloride, Amorgen K (trade name of an N-tetradecyl-N,N-betaine type surfactant, available from Dai-Ichi Kogyo Seiyaku Co., Ltd.), 2-alkyl-N-carboxyethyl-N-hydroxyethyl imidazolinium betaine and Rebon 15 (trade name of an alkyl imidazoline type one available from Sanyo Chemical Industries, Ltd.).

The content of the foregoing non-ionic and/or amphoteric surfactants in the composition preferably ranges from 0.05 to 15% by weight and more preferably 0.1 to 5% by weight on the basis of the total weight of the composition.

The light-sensitive composition used in the invention may comprise a printing out agent for obtaining a visible image immediately after imagewise exposure to light, a dye for coloring images and other fillers. A representative example of the printing out agent is a combination of a light-sensitive compound capable of releasing an acid through exposure to light with a salt-forming organic dye.

There are proposed various kinds of compounds as light-sensitive compounds capable of releasing acids through exposure and specific examples thereof are o-naphthoquinonediazide-4-sulfonic acid halides disclosed in U.S. Pat. No. 3,969,118; trihalomethyl-2-pyrone and trihalomethyltriazine disclosed in U.S. Pat. No. 4,160,671; various o-naphthoquinonediazide compounds disclosed in J.P. KOKAI No. Sho 55-62444; and 2-trihalomethyl-5-aryl-1,3,4-oxadiazole compounds disclosed in U.S. Pat. No. 4,279,982. On the other hand, the organic acids which change their color tones through the interactions with these photolytically decomposable substances are, for instance, diphenylmethane type, triarylmethane type, thiazine type, oxazine type, phenazine type, xanthene type, anthraquinone type, iminonaphthoquinone type and azomethine type dyes and specific examples thereof include Brilliant Green, Eosine, Ethyl Violet, Erythrocin B, Methyl Green, Crystal Violet, Basic Fuchsine, phenolphthalein, 1,3-diphenyltriazine, Alizarine Red S, thymolphthalein, Methyl Violet 2B, Quinaldine Red, Rose Bengale, Metanil Yellow, thymolsulfophthalein, Xylenol Blue, Methyl Orange, Orange IV, diphenyl thiocarbazone, 2,7-dichlorofluoresceine, Paramethyl Red, Congo Red, Benzopurpurine 4B, α-Naphthyl Red, Nile Blue A, phenacetaline, Methyl Violet, Malachite Green, Parafuchsine; Oil Blue #603, Oil Pink #312, Oil Red 5B, Oil Scarlet #308, Oil Red OG, Oil Red RR and Oil Green #502 (available from Orient Chemical Industries, Ltd.); Spiron Red BEH Special and Victoria Pure Blue BOH (available from Hodogaya Chemical Co., Ltd.); Patent Pure Blue (available from Sumitomo Mikuni Chemical Industries, Ltd.); Sudan Blue II (available from BASF Company); m-Cresol Purple, Cresol Red, Rhodamine B, Rhodamine 6G, Fast Acid Violet R, Sulforhodamine B, Auramine, 4-p-diethylaminophenyliminonaphthoquinone, 2-carboxyanilino-4-p-diethylaminophenyliminonaphthoquinone, 2-carbostearylamino-4-p-dihydroxyethylamino-phenyliminonaphthoquinone, p-methoxybenzoyl-p'-diethylamino-o'-methylphenyliminoacetanilide, cyano-p-diethylaminophenyliminoacetanilide, 1-phenyl-3-methyl-4-p-diethylaminophenylimino-5-pyrazoline and 1-β-naphthyl-4-p-diethylaminophenylimino-5-pyrazolone.

Particularly useful dyes are basic dyes such as Victoria Pure Blue and Ethyl Violet as disclosed in J.P. KOKAI No. Sho 62-293247 whose counter anions are replaced with those derived from organic sulfonic acids.

The PS plate of the present invention can be prepared by dissolving the foregoing components in an appropriate solvent, applying the resulting solution onto the surface of a substrate and then drying the layer applied.

Solvents used herein are, for instance, ethylene dichloride, cyclohexanone, methyl ethyl ketone, ethylene glycol monomethyl ether, ethylene glycol monoethyl ether, 2-methoxyethyl acetate, 1-methoxy-2-propanol, 1-methoxy-2-propyl acetate, toluene, ethyl acetate, methyl lactate, ethyl lactate, dimethylsulfoxide, dimethylacetamide, dimethylformamide, water, N-methylpyrrolidone, tetrahydrofurfuryl alcohol, acetone, diacetone alcohol, methanol, ethanol, isopropanol and diethylene glycol dimethyl ether, which may be used alone or in combination. The concentration (solid content) of the foregoing components is 2 to 50% by weight. In addition, the amount of the solution to be coated varies depending on intended applications. For instance, a solution having a solids content of 0.5 to 3.0 g/m² is preferably used for the preparation of a PS plate. The smaller the amount thereof coated, the greater the light-sensitivity of the resulting light-sensitive film, but the lower the physical properties thereof.

The light-sensitive composition used in the invention may further comprise, for the improvement of coating properties, a fluorine atom-containing surfactant as disclosed in U.S. Pat. No. 4,822,713. The amount thereof preferably ranges from 0.01 to 1% by weight and more preferably 0.05 to 0.5% by weight on the basis of the total weight of the composition.

The surface of the light-sensitive layer thus applied is preferably matted to reduce the time required for evacuation during contact exposure in a vacuum printing frame and to prevent the formation of an indistinct image during printing. The mat layer may be formed by methods disclosed in, for instance, J.P. KOKAI No. Sho 50-125805 and J.P. KOKOKU Nos. Sho 57-6582 and Sho 61-28986. Alternatively, it can likewise be formed by heat-fusing solid powder onto the surface of the light-sensitive layer as disclosed in J.P. KOKOKU No. Sho 62-62337.

Developers for the light-sensitive composition used in the invention are preferably alkaline aqueous solutions substantially free of any organic solvent. Specific examples of the alkaline agents used therein include sodium silicate, potassium silicate, lithium silicate, sodium hydroxide, potassium hydroxide, lithium hydroxide, sodium tertiary phosphate, sodium secondary phosphate, ammonium tertiary phosphate, ammonium secondary phosphate, sodium metasilicate, sodium carbonate, sodium bicarbonate, potassium bicarbonate and ammonia. The concentration of the alkaline agent in the developer ranges from 0.1 to 10% by weight and preferably 0.5 to 5% by weight.

Among these developers, preferred are those comprising alkali silicates such as potassium silicate, lithium silicate and sodium silicate since they permit the elimination of background contamination during printing. A developer preferably used comprises an alkali silicate having a molar ratio: $(SiO_2)/(M)$ ranging from 0.5 to 2.5 (wherein $(SiO_2)$ and $(M)$ represent the molar concentration of $SiO_2$ and that of the total alkali metal, respectively) and has an $SiO_2$ content of 0.8 to 8% by weight. Moreover, the developer may comprise, for instance, a water-soluble sulfite such as sodium sulfite, potassium sulfite or magnesium sulfite; and/or resorcin, methyl resorcin, hydroquinone or thiosalicylic acid. The preferred content of these compounds in the developer ranges from 0.002 to 4% by weight and more preferably 0.01 to 1% by weight.

Preferably, the developer further comprises at least one member selected from the group consisting of anionic and amphoteric surfactants as disclosed in J.P. KOKAI Nos. Sho 50-51324 and Sho 59-84241 and non-ionic surfactants as disclosed in J.P. KOKAI Nos. Sho 59-75255, Sho 60-111246 and Sho 60-213943, or a high molecular weight electrolyte as disclosed in J.P. KOKAI Nos. Sho 55-95946 and Sho 56-142528 for the improvement of the ability of wetting the light-sensitive layer and for ensuring high stability of development (development latitude). The surfactant can be added to the developer preferably in an amount of 0.001 to 2% by weight, in particular 0.003 to 0.5% by weight. The developer preferably comprises at least 20 mole% of potassium on the basis of the total molar amount of the alkali metals present in the developer since the use thereof accompanies formation of only a small amount of insoluble matter. The potassium content is more preferably not less than 90 mole% and most preferably 100 mole%.

The developer used in the invention may further comprise a small amount of an organic solvent such as an alcohol, a chelating agent as disclosed in J.P. KOKAI No. Sho 58-190952, a metal salt as disclosed in J.P. KOKOKU No. Hei 1-30139 and/or an antifoaming agent.

Light sources used in the imagewise exposure of the PS plate include, for instance, a carbon arc lamp, a mercury lamp, a xenon lamp, a tungsten lamp and a metal halide lamp.

The PS plate of the present invention may of course be treated by the methods disclosed in J.P. KOKAI Nos. Sho 54-8002, Sho 55-115045 and Sho 59-58431 to give a lithographic printing plate. More specifically, a PS plate which has been developed can be washed with water and then desensitized, or desensitized without water-washing, or treated with an aqueous solution containing an acid and then desensitized. Moreover, the alkali concentration of the developer is reduced due to consumption of alkali in proportion to the quantity of PS plates processed in the process for the development of a PS plate of this kind or absorption of carbon dioxide in the air observed when an automatic developing machine is operated over a long time. This leads to a reduction of the ability of the developer to process PS plates. In this case, a replenisher may be supplemented to recover the processing ability thereof as disclosed in J.P. KOKAI No. Sho 54-62004. The replenishment is preferably performed in the manner as disclosed in U.S. Pat. No. 4,882,246. In addition, the foregoing plate-making process is preferably carried out in an automatic developing machine as disclosed in J.P. KOKAI Nos. Hei 2-7054 (U.S. Pat. No. 4,952,958) and Hei 2-32357.

When undesirable portions of images are eliminated after imagewise exposure, development and water-washing or rinsing, it is preferred to use an erasing solution as disclosed in J.P. KOKOKU No. Hei 2-13293 (U.S. Pat. No. 4,396,703). Desensitizing gums optionally applied onto the processed PS plate in the final step of the plate-making process are preferably those disclosed in J.P. KOKOKU Nos. Sho 62-16834 (U.S. Pat. No. 4,348,954), Sho 62-25118 (U.S. Pat. No. 4,268,613) and Sho 63-52600 and J.P. KOKAI Nos. Sho 62-7595 (U.S. Pat. No. 4,731,119), Sho 62-11693 (U.S. Pat. No. 4,719,172) and Sho 62-83194 (U.S. Pat. No. 4,762,772). Moreover, if a PS plate is burned after it is imagewise exposed, developed, washed with water or rinsed, optionally erased and washed with water, the surface of the plate is preferably treated with a surface-conditioning solution as disclosed in J.P. KOKOKU Nos. Sho 61-2518 (U.S. Pat. No. 4,294,910) and Sho 55-28062 (U.S. Pat. No. 4,063,507) and J.P. KOKAI Nos. Sho 62-31859 (U.S. Pat. No. 4,762,771) and Sho 61-159655.

The PS plate of the present invention permits the complete removal of any pasting marks formed on the resulting lithographic printing plate even with an erasing solution substantially free of hydrofluoric acid. Moreover, ink does not adhere to the portions on which the pasting marks are formed even if the plate is burned after the plate-making process. Further, the plate has a high development latitude and, therefore, any trouble such as dissolution of images in a developer does not arise even if the developer is used at an elevated temperature.

The present invention will hereinafter be described in more detail with reference to the following non-limitative working Examples and the effects practically attained by the invention will also be discussed in detail. In the following Examples and Comparative Examples, the term "%" means "% by weight" unless otherwise specified.

Examples 1 to 3 and Comparative Examples a to c

An aluminum plate having a thickness of 0.30 mm was surface-grained with a nylon brush and an aqueous suspension of 400 mesh pumice stone and then sufficiently washed with water. The plate was etched by immersing in a 10% sodium hydroxide solution at 70° C. for 60 seconds, washed with running water, then neutralized and washed with a 20% nitric acid solution and washed with water. The plate was then electrolytically surfaceroughened in a 1% aqueous solution of nitric acid at an anodic voltage, $V_A$, of 12.7 V such that the quantity of electricity at the anode was 160 coulomb/dm$^2$ using a sinusoidal alternating wave current. At this stage, the surface roughness of the plate was determined and found to be 0.6μ (expressed in terms of Ra unit). Then it was desmutted by immersing in a 30% aqueous sulfuric acid solution at 55° C. for 2 minutes and anodized in a 20% aqueous sulfuric acid solution at a current density of 2 A/dm$^2$ so that the thickness of the resulting anodized layer was 2.7 g/m$^2$ to give a substrate.

A solution (A) for underlying coating having the following composition was applied onto the surface of the substrate thus obtained and dried at 80° C. for 30 seconds. The coated amount of the solution was found to be 30 mg/m$^2$ (weighed after drying).

| Solution (A) for Underlying Coating | |
|---|---|
| Component | Amount (g) |
| aminoethylphosphonic acid | 0.1 |
| phenylphosphonic acid | 0.15 |
| β-alanine | 0.1 |
| methanol | 40 |
| pure water | 60 |

Then the following light-sensitive solution was applied onto the underlying coating and dried at 100° C. for one minute to give a PS plate. The coated amount of the solution was found to be 1.7 g/m$^2$ (weighed after drying).

| Light-Sensitive Solution | |
|---|---|
| Component | Amount (g) |
| light-sensitive substance listed in Table 1 | 0.43 |
| cresol-formaldehyde novolak resin (m—/p— = 6.4; average molecular weight 1100; content of unreacted cresol 0.5%) | 1.1 |
| m-cresol-formaldehyde resin (weight-average molecular weight 1700; number-average molecular weight 600; content of unreacted cresol 1%) | 0.3 |
| N-(p-aminosulfonylphenyl)acrylamide/ n-butyl acrylate/diethylene glycol monomethyl ether methacrylate (40:40:20) copolymer | 0.2 |
| p-n-octylphenol-formaldehyde resin | 0.02 |
| 1,2-naphthoquinonediazide-4-sulfonic acid chloride | 0.01 |
| benzoic acid | 0.02 |
| tetrahydrophthalic anhydride | 0.05 |
| 4-(p-N,N-di(ethoxycarbonyl)aminophenyl)-2,6-bis(trichloromethyl)-s-triazine | 0.02 |
| 4-(p-N-(p-hydroxybenzoyl)aminophenyl)-2,6-bis(trichloromethyl)-s-triazine | 0.02 |
| 2-trichloromethyl-5-(4-hydroxystyryl)-1,3,4-oxadiazole | 0.01 |
| Victoria Pure Blue BOH whose counter ion is replaced with 1-naphthalenesulfonate ion | 0.01 |
| Ethyl Violet whose counter ion is replaced with 6-hydroxynaphthalenesulfonate ion | 0.01 |
| Megafac F-176 (a fluorine atom-containing surfactant available from Dainippon Ink and Chemicals, Inc.) | 0.06 |

-continued

| Light-Sensitive Solution | |
|---|---|
| Component | Amount (g) |
| methyl ethyl ketone | 25 |

In a vacuum printing frame, the PS plates thus prepared were imagewise exposed, for 60 seconds, to light from a halide lamp through an original prepared by pasting three positive films on a transparent base with a cellophane adhesive tape and then processed in an automatic developing machine charged with a developer, DP-4 (diluted 8 times), and a rinsing solution, FR-3 (diluted 7 times) (both available from Fuji Photo Film Co., Ltd.). Film edge-marks and adhesive tape-marks observed on the resulting lithographic printing plate was then erased with a writing brush dampened with an erasing solution, PR-1 available from Fuji Photo Film Co., Ltd., then the plate was washed with water, the plate surface was wiped with a cloth dampened with a surface-conditioning solution for burning, BC-3 (available from Fuji Photo Film Co., Ltd.), and the plate was processed at 260° C. for 7 minutes in a burning device BP-1300. Then the plate surface was treated with a gum GU-7 available from Fuji Photo Film Co., Ltd. diluted 2 times with water, the plate was allowed to stand for one day and then mounted on a printing press, Heidel KOR-D to prepare copies. The resulting copies were visually examined for the presence of background contamination due to the film edge-marks and adhesive tape-marks which would have been erased before.

The development in the foregoing processing was performed at 25° C. Separately, it was also carried out at 40° C. and the light-sensitive layer on the image areas was visually examined for the dissolution thereof in the developer.

The results thus obtained are summarized in the following Table 1. These results clearly indicate that the positive-working PS plates of the present invention exhibit excellent erasing properties and have high development latitude as compared with Comparative Examples.

TABLE 1

| Ex. No. | Light-sensitive Substance Used | Contamination of Copies due to Marks[1] | Loss of Film visually Observed[2] |
|---|---|---|---|
| 1 | ester of polyhydroxy compound [I-a] with 1,2-diazonaphthoquinone-5-sulfonyl chloride (degree of esterification: 79%) | None | slight |
| 2 | ester of polyhydroxy compound [I-b] with 1,2-diazonaphthoquinone-5-sulfonyl chloride (degree of esterification: 82%) | None | slight |
| 3 | ester of polyhydroxy compound [I-n] with 1,2-diazonaphthoquinone-5-sulfonyl chloride (degree of esterification: 79%) | None | None |
| a* | ester of pyrogallol-acetone resin with 1,2-diazonaphthoquinone-5-sulfonyl chloride (the compound disclosed in Ex. 1 of U.S. Pat. No. 3,635,709) | severely contaminated | almost half of the film was lost |

TABLE 1-continued

| Ex. No. | Light-sensitive Substance Used | Contamination of Copies due to Marks[1] | Loss of Film visually Observed[2] |
|---|---|---|---|
| b* | ester of pyrogallol-formaldehyde resin with 1,2-diazonaphthoquinone-5-sulfonyl chloride (the compound disclosed in Ex. 1 of U.S. Pat. No. 3,046,120) | severely contaminated | a great loss |
| c* | ester of 2,2,4,4'-tetrahydroxybenzophenone with 1,2-diazonaphthoquinone-5-sulfonul chloride (degree of esterification: 77%) | severely contaminated | almost half of the film was lost |

[1] Background contamination of the copies due to the film edgemarks and/or adhesive tape-marks.
[2] Loss of films on image areas visually observed when each printing plate was developed at a temperature of 40° C.
*Comparative Example

We claim:

1. A presensitized plate for use in making a lithographic printing plate comprising a surface-grained and anodized aluminum plate provided thereon with a light-sensitive layer of a composition comprising in admixture at least one light-sensitive substance and an alkali-soluble resin wherein the light-sensitive substance is present in an amount of from 5 to 100 parts by weight based on the total amount of alkali-soluble resin and is a 1,2 (and/or 2,1)-naphthoquinonediazide-5-(and/or -4-)sulfonic acid ester of a polyhydroxy compound represented by the following general formula (I):

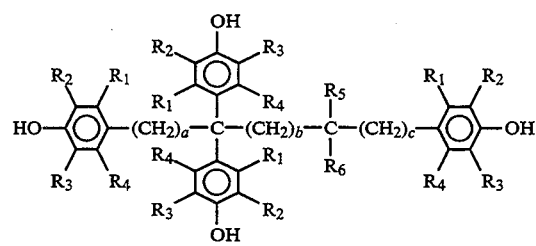

wherein substituents $R_1$ to $R_4$ are the same or different and each represents a hydrogen atom, a hydroxyl group, a halogen atom, an alkyl group, an alkoxy group or an alkenyl group; $R_5$ and $R_6$ each represents a hydrogen atom, an alkyl group or a group:

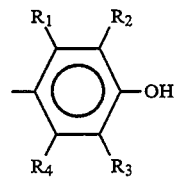

(wherein $R_1$ to $R_4$ are the same as those defined above), a and c each represents 0 or 1 and b represents 0 or an integer ranging from 1 to 4.

2. The presensitized plate of claim 1 wherein the substituents $R_1$ to $R_4$ of Formula (I) each represents a hydrogen atom, a hydroxyl group, a chlorine, bromine or iodine atom, an alkyl group having 1 to 4 carbon atoms, an alkoxy group having 1 to 4 carbon atoms or an alkenyl group having 1 to 4 carbon atoms; and $R_5$ and $R_6$ each represents a hydrogen atom, an alkyl group having 1 to 4 carbon atoms or a group:

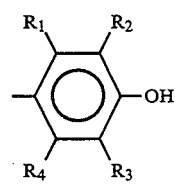

(wherein $R_1$ to $R_4$ are the same as those defined above).

3. The presensitized plate of claim 1 wherein the amount of the light-sensitive compound ranges from 10 to 50 parts by weight on the basis of the amount of the alkali-soluble resin.

4. The presensitized plate of claim 1 wherein the alkali-soluble resin has a weight-average molecular weight ranging from 500 to 20,000 and a number-average molecular weight ranging from 200 to 6,000.

5. The presensitized plate of claim 1 wherein the amount of the alkali-soluble resin is not more than 80% by weight on the basis of the total weight of the composition.

6. The presensitized plate of claim 1 wherein the composition further comprises a cyclic acid anhydride, a phenol and/or an organic acid, in an amount ranging from 0.1 to 5% by weight on the basis of the total weight of the composition.

7. The presensitized plate of claim 1 wherein the composition further comprises a non-ionic or amphoteric surfactant in an amount ranging from 0.1 to 5% by weight on the basis of the total weight of the composition.

8. The presensitized plate of claim 1 wherein the composition further comprises a printing out agent for obtaining a visible image immediately after exposure, a dye as an agent for coloring images and/or a filler.

9. The presensitized plate of claim 1 wherein the composition further comprises a fluorine atom-containing surfactant in an amount ranging from 0.05 to 0.5% by weight on the basis of the total weight of the composition.

* * * * *